US009655923B2

United States Patent
Yang et al.

(10) Patent No.: US 9,655,923 B2
(45) Date of Patent: May 23, 2017

(54) USE OF NANO METAL IN PROMOTING NEURITE OUTGROWTH AND TREATMENT AND/OR PREVENTION OF NEUROLOGICAL DISORDERS

(71) Applicant: GNT Biotech & Medicals Corporation, Taipei (TW)

(72) Inventors: Ying-Chen Yang, Taipei (TW); Chia-Nan Chen, Taipei (TW); Li-Ling Chi, Taipei (TW)

(73) Assignee: GNT Biotech & Medicals Corporation, Taipei (TW)

( * ) Notice: Subject to any disclaimer, the term of this patent is extended or adjusted under 35 U.S.C. 154(b) by 0 days.

(21) Appl. No.: 14/800,997

(22) Filed: Jul. 16, 2015

(65) Prior Publication Data
US 2016/0015742 A1 Jan. 21, 2016

Related U.S. Application Data

(60) Provisional application No. 62/025,176, filed on Jul. 16, 2014.

(51) Int. Cl.
| | |
|---|---|
| B82Y 5/00 | (2011.01) |
| A61K 33/24 | (2006.01) |
| A61K 9/00 | (2006.01) |
| B22F 1/00 | (2006.01) |
| A61K 9/14 | (2006.01) |
| A61K 45/06 | (2006.01) |
| A61K 33/06 | (2006.01) |
| A61K 33/34 | (2006.01) |
| A61K 33/38 | (2006.01) |

(52) U.S. Cl.
CPC ............ *A61K 33/24* (2013.01); *A61K 9/0019* (2013.01); *A61K 9/14* (2013.01); *A61K 33/06* (2013.01); *A61K 33/34* (2013.01); *A61K 33/38* (2013.01); *A61K 45/06* (2013.01); *B22F 1/00* (2013.01); *B82Y 5/00* (2013.01); *C01P 2004/64* (2013.01)

(58) Field of Classification Search
CPC ....... A82Y 5/00; B22F 1/0018; C01P 2004/64
See application file for complete search history.

(56) References Cited

U.S. PATENT DOCUMENTS

2010/0068240 A1 3/2010 Chiu et al.

OTHER PUBLICATIONS

Alon et al (Silver Nanoparticles Promote Neuronal Growth, Procedia Engineering 59 (2013) 25-29.*
Pisanic et al.; Neurotoxicity of Iron Oxide Nanoparticle Internalization in Growing, Neurons, Biomaterials 28 (2007) 2572-2581.*
Office action issued on Apr. 25, 2016 by the Taiwan Intellectual Property Office for Taiwan application 104123188.

(Continued)

*Primary Examiner* — Carlos Azpuru
(74) *Attorney, Agent, or Firm* — WPAT, P.C., Intellectual Property Attorneys; Anthony King

(57) ABSTRACT

The invention relates to a method of using metal nanoparticle or metallic particle to promote neurite outgrowth and treat and/or prevent neurological disorders. Particularly, the method of the invention uses gold nanoparticles or gold particles to promote neurite outgrowth and treat and/or prevent neurological disorders.

10 Claims, 14 Drawing Sheets

(56) References Cited

OTHER PUBLICATIONS

English abstract translation of the Office action issued on Apr. 25, 2016 by the Taiwan Intellectual Property Office for Taiwan application 104123188.
Noa Alon et al., Substrates coated with silver nanoparticles as a neuronal regenerative material; International Journal of Nanomedicine, 2014, vol. 9 (Supp. 1), pp. 23-31.
Search report from the EPO issued on Mar. 16, 2016 for corresponding European application 15177107.8.
Jung, Seungmoon et al., Intracellular Gold Nanoparticles Increase Neuronal Excitability and Aggravate Seizure Activity in the Mouse, BrainPLOS One, vol. 9, Issue 3, e91360.

* cited by examiner

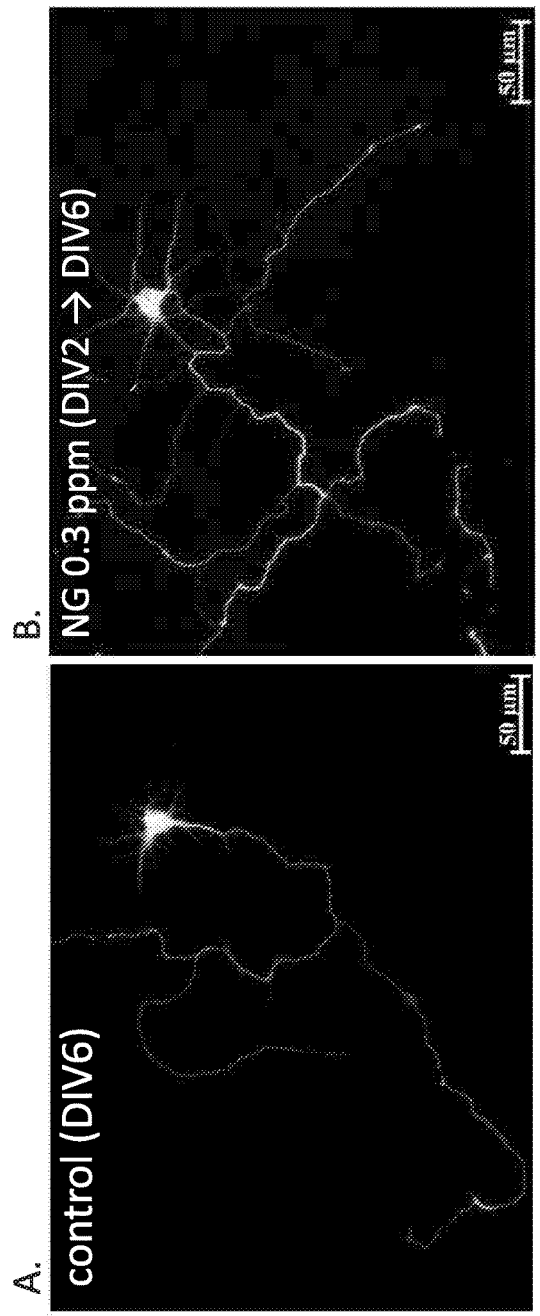

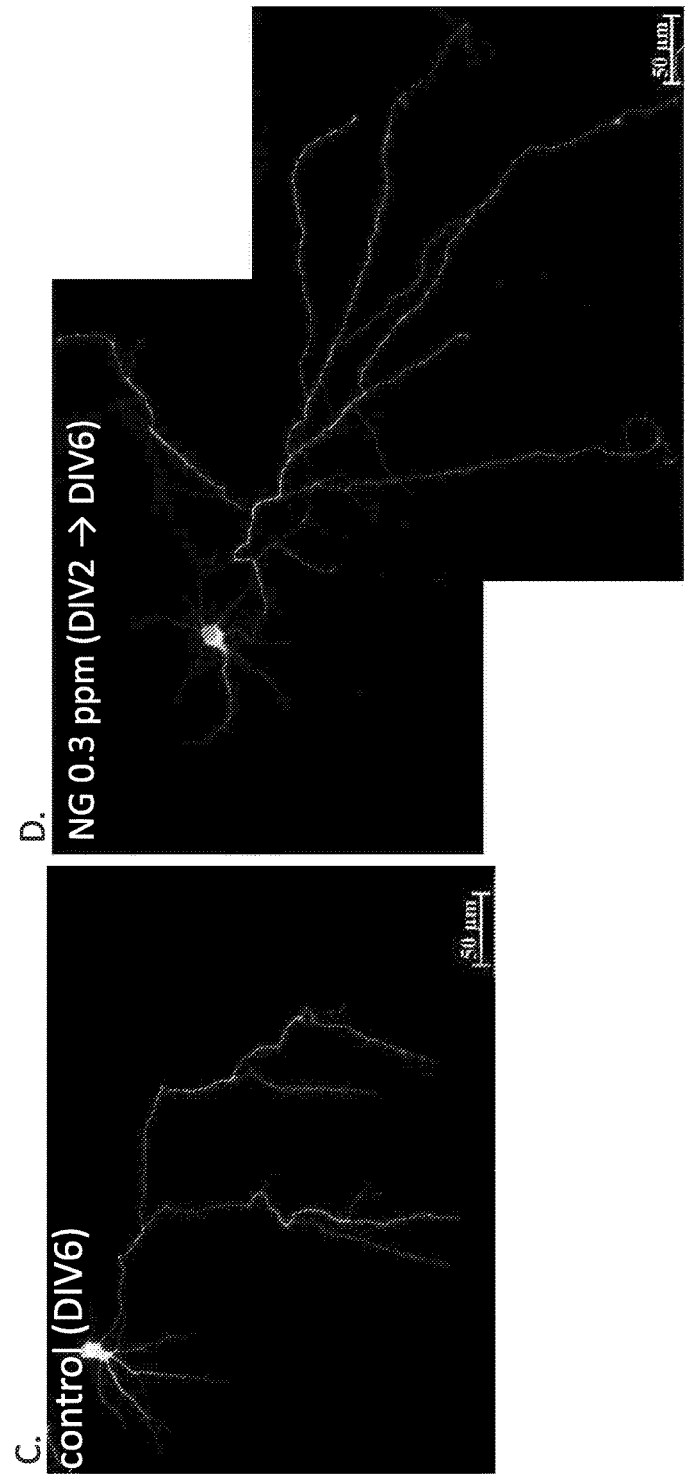

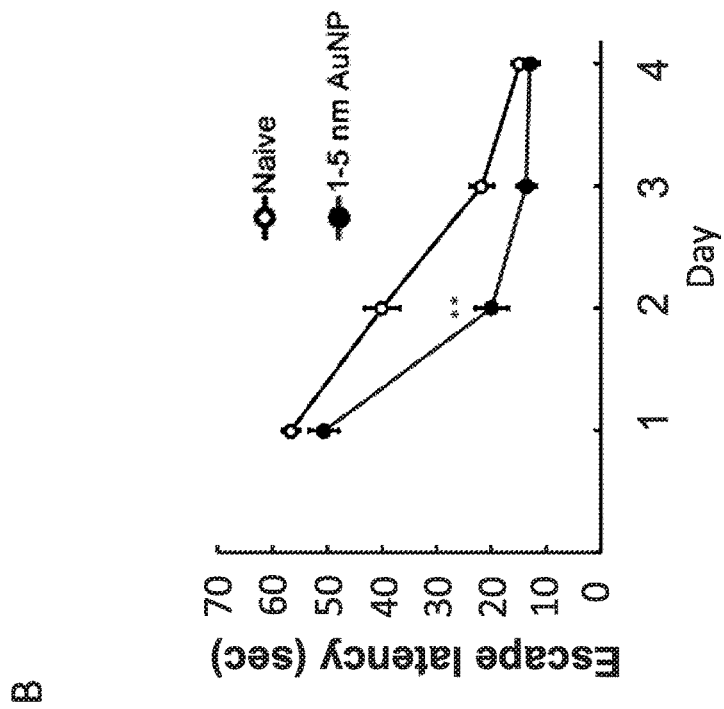
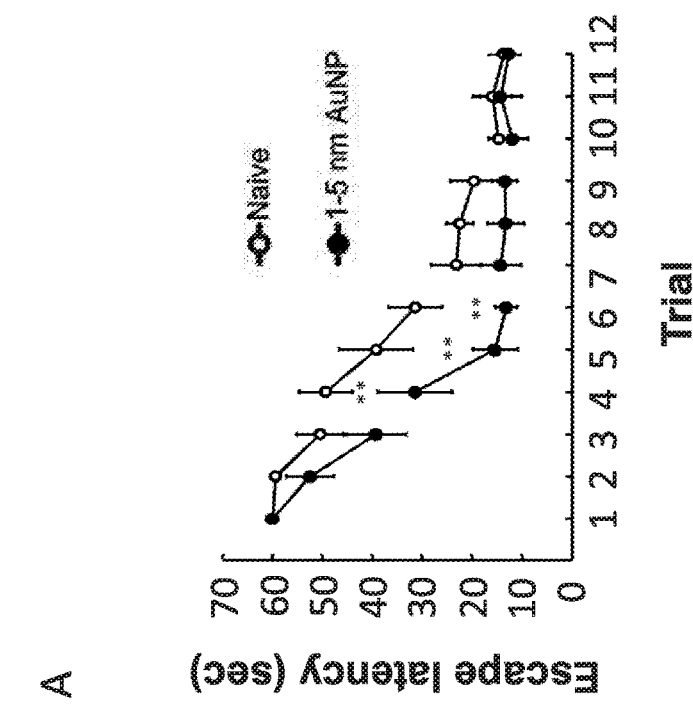
Fig. 7

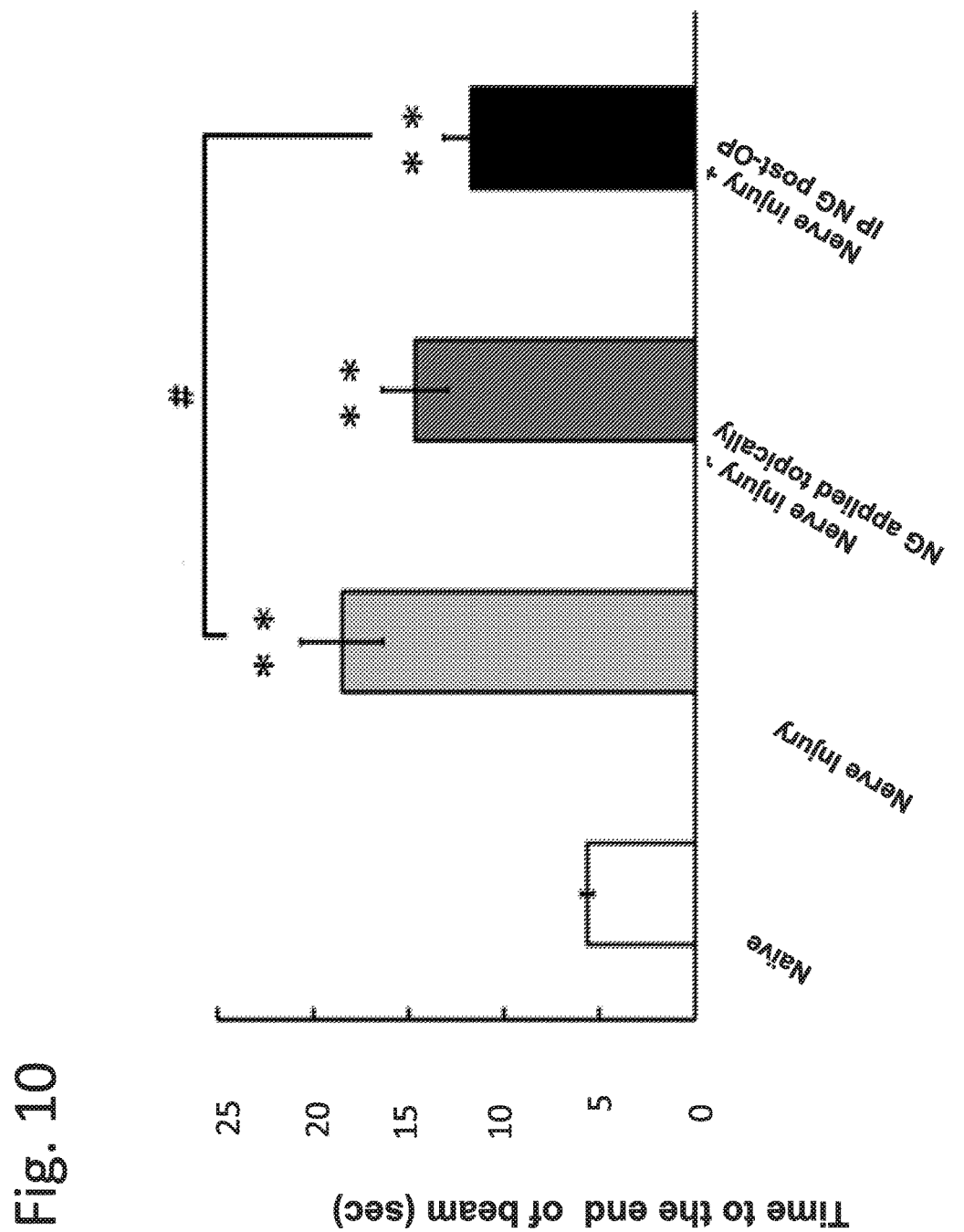

USE OF NANO METAL IN PROMOTING NEURITE OUTGROWTH AND TREATMENT AND/OR PREVENTION OF NEUROLOGICAL DISORDERS

FIELD OF THE INVENTION

The invention relates to a method of using metallic nanoparticles or metallic particles to promote neurite outgrowth and treat and/or prevent neurological disorders. Particularly, the method of the invention uses gold nanoparticles or gold particles to promote neurite outgrowth and treat and/or prevent neurological disorders.

BACKGROUND OF THE INVENTION

Neurological disorders include acute brain or cord injury such as stroke and chronic aging and several neurodegenerative disorders such as Alzheimer's disease, Parkinson's disease and Huntington's disease. Neurodegeneration relates to the progressive loss of structure or function of neurons, including death of neurons. Many neurodegenerative diseases occur as a result of neurodegenerative processes. Currently, no effective therapies exist that provide either protection or restoration of neuronal function for neurodegenerative diseases. Many clinical efforts to provide such benefits by infusion of neurotrophic factors have failed in spite of robust effects in preclinical assessments. One important reason for these failures is the difficulty, due to blood-brain-barrier diffusion limits, of providing these protein molecules in sufficient amounts to the intended cellular targets in the central nervous system. A great need exists for the development of a novel therapeutic approach that promotes an axonal regenerative response where axons are able to regrow, reach their targets, and restore function.

Metallic nanoparticles have been intensely studied due to their unique optical, electrical and catalytic properties. To utilize and optimize chemical and physical properties of nano-sized metal particles, a large spectrum of research has been focused on control of size and shape which is crucial in tuning their properties. Several approaches are in practice to synthesize metallic nanoparticles such as UV irradiation, laser ablation, aerosol technology, lithography, ultrasonic fields, and photochemical reduction techniques. US 20100068240 discloses implantable nerve regeneration conduits that mainly comprise a biodegradable polymer and a metal, wherein nanogold is used to enhance the physical strength of the conduit or facilitate nerve regeneration by increasing the amount of BDNF and GDNF released from glia cells. However, the nanometal used in US 20100068240 is to enhance the strength of the implantable conduit and stimulate glia cells to release BDNF and GDNF; however, this prior art reference neither teaches nor suggests the direct increase of neuron growth and treatment of neurological disorders by metal nanoparticles themselves. Seungmoon Jung et al. disclose that intracellular gold nanoparticles increase excitability and aggravation, whereas the reference shows that intracellular AuNPs led to abnormal firing patterns and aggravated epileptic activity under pathological conditions, thus suggesting a possibility that intracellular AuNPs can cause or worsen neuronal dysfunction or damage in the brain (Seungmoon Jung et al., PLOS ONE, Vol. 9, Issue 3, e91360).

Therefore, there is still a need to develop an approach to promote neuron growth/outgrowth and treat and/or prevent neurological disorders.

SUMMARY OF THE INVENTION

The invention provides a method for improving neurite outgrowth, the method comprising exposing the neuron to an extent to which a metallic nanoparticle or a metallic particle formed by stacking up a plurality of the metallic nanoparticles acts to promote neurite outgrowth. In one embodiment, the method comprises contacting the neuron with the metallic nanoparticle or the metallic particle. In another embodiment, the metallic nanoparticle or metallic particle is selected from the group consisting of silver nanoparticle or silver particle, gold nanoparticle or gold particle, platinum nanoparticle or platinum particle, palladium nanoparticle or palladium particle, aluminum nanoparticle or aluminum particle, nickel nanoparticle or nickel particle, cobalt nanoparticle or cobalt particle, copper nanoparticle or copper particle, and combinations thereof.

The invention also provides a method for treating and/or preventing a neurological disorder, the method comprising administering an effective amount of a metallic nanoparticle or metallic particle formed by stacking up a plurality of the metallic nanoparticles to a subject, thereby treating and/or preventing a neurological disorder.

In one another embodiment, the metallic nanoparticle can be administered by direct contact, oral administration, inhalation, subcutaneous administration (S.C.), intravenous administration (I.V.), intraperitoneal administration (I.P.), intramuscular administration (I.M.), intrathecal injection, intranasal, topical application, or localized administration.

In a further embodiment, the metallic nanoparticle or particle is combined with a targeting agent passing the blood brain barrier.

In a further embodiment, the neurological disorder is multiple sclerosis, sciatic nerve defect, an injury to the nervous system, amyotrophic lateral sclerosis (ALS); trigeminal neuralgia; glossopharyngeal neuralgia; Bell's palsy; myasthenia gravis; muscular dystrophy; progressive muscular atrophy; primary lateral sclerosis (PLS); pseudobulbar palsy; progressive bulbar palsy; spinal muscular atrophy; progressive bulbar palsy; inherited muscular atrophy; invertebrate disk syndromes (e.g., herniated, ruptured, and prolapsed disk syndromes); cervical spondylosis; plexus disorders; thoracic outlet destruction syndromes; peripheral neuropathies; prophyria; mild cognitive impairment; Alzheimer's disease; Huntington's disease; Parkinson's disease; Parkinson-plus syndromes (e.g., multiple system atrophy, progressive supranuclear palsy, and corticobasal degeneration); dementia with Lewy bodies; frontotemporal dementia; demyelinating diseases (e.g., Guillain-Barre syndrome and multiple sclerosis); Charcot-Marie-Tooth disease (CMT; also known as Hereditary Motor and Sensory Neuropathy (HMSN); Hereditary Sensorimotor Neuropathy (HSMN) and Peroneal Muscular Atrophy); prion disease (e.g., Creutzfeldt-Jakob disease, Gerstmann-Straussler-Scheinker syndrome (GSS), fatal familial insomnia (FFI) and bovine spongiform encephalopathy (BSE, commonly known as mad cow disease)); Pick's disease; epilepsy; AIDS demential complex (also known as HIV dementia, HIV encephalopathy, and HIV-associated dementia); peripheral neuropathy and neuralgia caused by diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, or amyloidosis; peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

The invention also provides a medical device, comprising metallic nanoparticles or metallic particles formed by stacking up a plurality of the metallic nanoparticles in an amount sufficient to treat and/or prevent a neurological disorder. The invention also provides a method for treating and/or preventing a neurological disorder, the method comprising using a medical device containing an effective amount of metallic nanoparticles in a subject, thereby treating and/or preventing a neurological disorder.

BRIEF DESCRIPTION OF THE DRAWING

FIG. 10 shows the times took for the rats to traverse the beam.

DETAILED DESCRIPTION OF THE INVENTION

Figure 1:
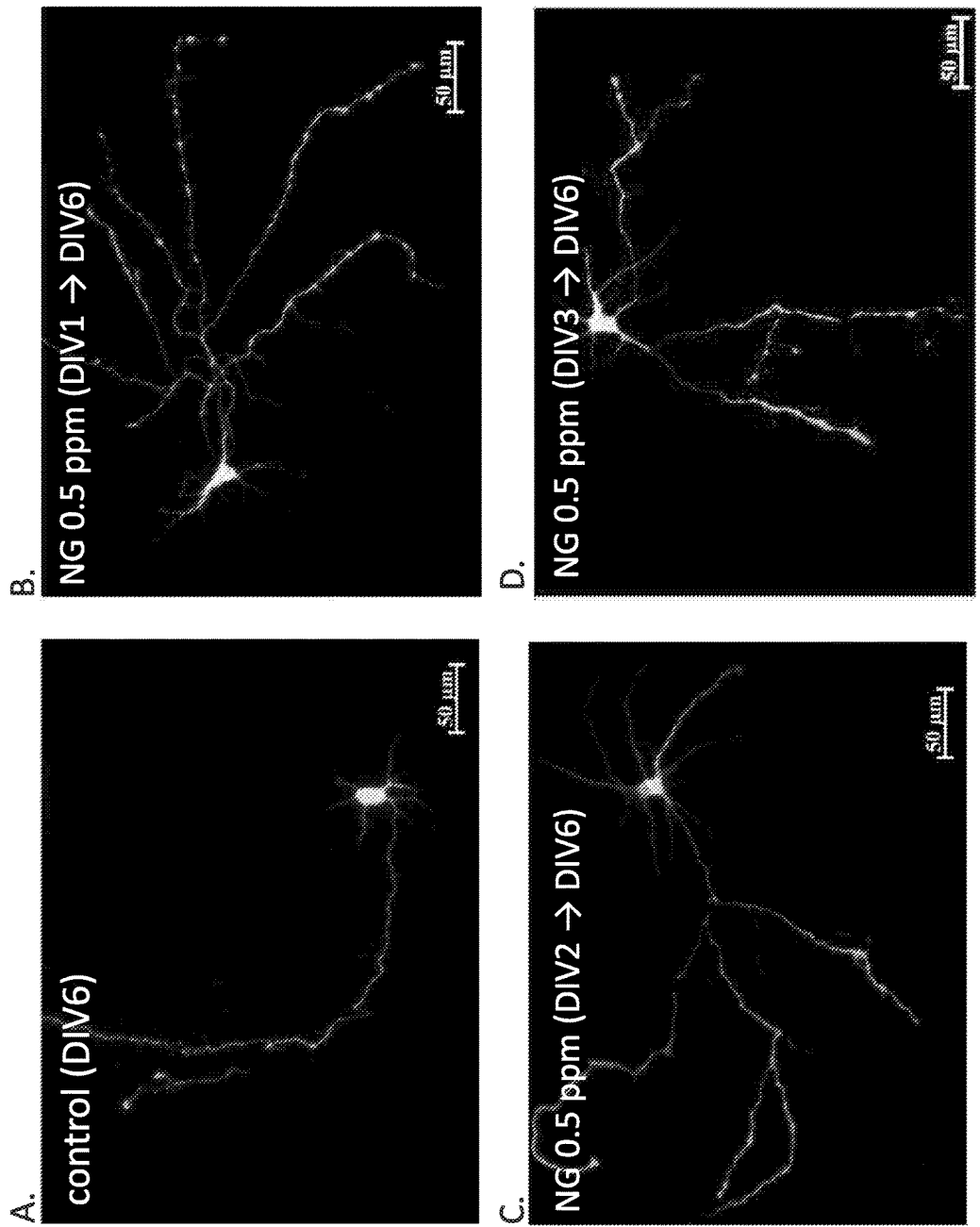
FIGS. 1A to 1D show immunofluorescence staining results of neurite outgrowth assay using 0 and 0.5 ppm of nanoparticles on different days (A: control group; and B to D: gold nanoparticle-treated neurons on the first day (DIV 1), the second day (DIV2) and third day (DIV3), respectively).

The invention is based on the discovery that metallic nanoparticles or metallic particles can promote neurite outgrowth by serving as a neurotrophic factor and promoting the outgrowth of axons and dendrites. In view of the fact that the metallic nanoparticles or particles can serve as a neurotrophic factor itself, the metallic nanoparticles or particles can repair and/or treat and/or prevent neurological disorders such as neurodegenerative disease and brain or cord injury.

In one aspect, the invention provides a method for improving neurite outgrowth, the method comprising exposing the neuron to an extent to which a metallic nanoparticle or a metallic particle formed by stacking up a plurality of the metallic nanoparticles acts to promote neurite outgrowth. Preferably, the method comprises contacting the neuron with the metallic nanoparticle or the metallic particle.

In another aspect, the invention provides a method for treating and/or preventing a neurological disorder, the method comprising administering an effective amount of metallic nanoparticles or metallic particles formed by stacking up a plurality of the metallic nanoparticles to a subject thereby treating and/or preventing a neurological disorder.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference.

It is to be understood that both the foregoing general description and the following detailed description are illustrative and explanatory, and are not restrictive of the subject matter as claimed. In this application, the use of the singular includes the plural, the article "a" or "an" means "at least one," and the use of "or" means "and/or", unless specifically stated otherwise. Furthermore, the use of the term "including," as well as other forms, such as "includes" and "included", is not limiting. Also, terms such as "element" or "component" encompass both elements or components comprising one unit and elements or components that comprise more than one unit unless specifically stated otherwise.

As used herein, "metallic nanoparticle" refers to a nano-sized structure made by metal element in which at least one of its phases has one or more dimensions (length, width or thickness) in the nanometer size range. The "metallic particle" as used herein refers to a metal particle stacked up by a plurality of the metallic nanoparticles.

As used herein, "axon regeneration" means the regrowth, regeneration or sprouting of new axons from a living neuron cell body.

As used herein, "neurological disorders" means any physiological dysfunction or death of neurons present in the central nervous system or peripheral nervous system or caused by glia cell dysfunction. A non-limited list of such disorders comprises multiple sclerosis, sciatic nerve defect, brain or cord injury, dementia, frontotemporal lobe dementia, Alzheimer's disease, Parkinson's disease, Huntington's disease, prion diseases, neuronopathies and motor neuron disorders. "Neuronopathies" are characterized by neuronal cell death of motor neurons or sensory neurons, and hence neuronopathies can be subdivided into motor and sensory neuron disorders.

As used herein, "neurodegenerative disease" refers to the progressive loss of structure or function of neurons or physical degeneration including loss (death) of axons. Neurodegenerative diseases include Parkinson's disease, Alzheimer's disease, Huntington's disease and brain and spinal cord injuries as well as stroke.

As used herein, "subject", "individual" or "patient" is used interchangeably to refer to a vertebrate, preferably a mammal, more preferably a human. Mammals include, but are not limited to, murines, simians, humans, farm animals, sport animals, and pets. Tissues, cells and their progeny of a biological entity obtained in vitro or cultured in vitro are also encompassed.

As used herein, "treatment" or "treating" or "ameliorating" are used interchangeably. These terms refer to an approach for obtaining beneficial or desired results including, but not limited to, therapeutic benefit and/or a prophylactic benefit. Therapeutic benefit pertains to eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the metallic nanoparticles may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective metallic nanoparticle after the inductive event but prior to the clinical appearance or reappearance of the disease; inhibiting the disease, that is, arresting the development of clinical symptoms by administration of a metallic nanoparticle after initial appearance of the symptoms; preventing a recurrence of the disease and/or relieving the disease, that is, causing the regression of clinical symptoms by administration of a protective metallic nanoparticle after the initial appearance of the symptoms.

As used herein, "promote" or "increase", or "promoting" or "increasing" are used interchangeably. These terms refer to the increase in a measured parameter in a treated cell (tissue or subject) in comparison to an untreated cell (tissue or subject). A comparison can also be made of the same cell or tissue or subject between before and after treatment. The increase is sufficient to be detectable. In some embodiments, the increase in the treated cell is at least about 10%, 20%, 30%, 40%, 50%, 60%, 70%, 80%, 90%, 1-fold, 2-fold, 3-fold, 4-fold or more in comparison to an untreated cell.

As used herein, "inhibit," "prevent" or "reduce," or "inhibiting," "preventing" or "reducing" are used interchangeably. These terms refer to the decrease in a measured parameter in a treated cell (tissue or subject) in comparison to an untreated cell (tissue or subject). A comparison can also be made of the same cell or tissue or subject between before and after treatment. The decrease is sufficient to be detectable. In some embodiments, the decrease in the treated cell is at least about 10%, 20%, 30%, 40%, 50%, 60%, 70%, 80%, 90%, or completely inhibited in comparison to an untreated cell. In some embodiments the measured parameter is undetectable (i.e., completely inhibited) in the treated cell in comparison to the untreated cell.

As used herein, the term "neuron" includes a neuron and a portion or portions thereof (e.g., the neuron cell body, an axon, or a dendrite). The term "neuron" denotes nervous system cells that include a central cell body or soma and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment or methods according to the invention include cerebellar granule neurons, dorsal root ganglion neurons, and cortical neurons.

As used herein, "neurite" refers to any process growing out of a neuron. The term neurite as used herein encompasses all such cell processes (including both axon and dendrite) growing out of a neuron.

As used herein, "neurite outgrowth" refers to the process of cells growing out of a neuron, or to the cells comprising an outgrowth from a neuron, including, but not limited to elongation, branching and/or regeneration of neurites.

As used herein, "therapeutically effective amount" means an amount sufficient to treat a subject afflicted with a disease (e.g., a neurodegenerative disease) or to alleviate a symptom or a complication associated with the disease.

As used herein, "pharmaceutical composition" refers to the combination of an active agent (e.g., withanolide) with a carrier, inert or active, making the composition especially suitable for therapeutic use.

As used herein, "subject" refers to either a human or non-human animal.

Metallic Nanoparticles

The metallic nanoparticles are nano scale. The nano-metal particles preferably include a metal element selected from the group consisting of silver, gold, platinum, palladium, aluminum, nickel, cobalt, copper, and combinations thereof. They may be prepared according to UV irradiation, laser ablation, aerosol technology, lithography, ultrasonic fields, and photochemical reduction techniques known in the art. In one embodiment, the metallic nanoparticles are those prepared according to the manufacturing systems and methods disclosed in Taiwan Patent No. 1430858. Particularly, the metallic nanoparticles of Taiwan Patent No. 1430858 are prepared according to the process comprising steps of: (1) processing a metal material with purity of 99.99% to form a thin metal film with thickness less than 0.3 µm; (2) placing the thin metal film in a circulating conveyor belt in a first closed container with inert gas inside; (3) transporting the thin metal film into the plasma ablation chamber using a closed type circulating conveyor belt for microwave heating and sintering in order to be melted and create nano metal particles; (d) transporting the nano metal particles to a second closed container using the circulating conveyor belt, and cooling the particles by the cooling processor to form a suspension in a liquid; and (e) collecting the suspended nano metal particles to obtain the required high-purity nano particles metal.

The size of metallic nanoparticles used in the present invention can be between about 1 nm and about 1000 nm, preferably about 1 nm to about 400 nm; preferably, about 1 nm to about 350 nm, about 1 nm to about 300 nm, about 1 nm to about 250 nm, about 1 nm to about 200 nm, about 1 nm to about 100 nm, about 1 nm to about 50 nm, about 1 nm to about 30 nm, about 1 nm to about 20 nm, about 1 nm to about 10 nm, about 1 nm to about 5 nm, about 20 nm to about 350 nm, about 20 nm to about 300 nm, about 20 nm to about 250 nm, about 20 nm to about 200 nm, about 20 nm to about 150 nm, about 20 nm to about 100 nm or about 20 nm to about 80 nm; more preferably, about 1 nm to about 20 nm or about 1 nm to about 5 nm.

In one embodiment, the metallic nanoparticles can stack up to form metallic particles. The metallic particles also can be used for treating and/or preventing a neurological disorder.

It will be appreciated that the amount of the metallic nanoparticles or metallic particles required for use in promotion or treatment will vary, not only with the particular nanoparticle selected but also with the route of administration, the nature of the condition for which treatment is required, and the age and condition of the patient. In one embodiment, the metallic nanoparticles can be administered to a subject in a range from about 0.01 µg/kg/day to about 2,000 µg/kg/day or about 0.01 µg/kg/day to about 1,000 µg/kg/day or about 0.01 µg/kg/day to about 500 µg/kg/day or about 0.01 µg/kg/day to about 250 µg/kg/day or about 0.01 µg/kg/day to about 125 µg/kg/day or about 0.01 µg/kg/day to about 100 µg/kg/day or about 0.01 µg/kg/day to about 75 µg/kg/day or about 0.01 µg/kg/day to about 50 µg/kg/day or about 0.01 µg/kg/day to about 25 µg/kg/day or about 0.01 µg/kg/day to about 10 µg/kg/day or about 0.01 µg/kg/day to about 5 µg/kg/day; preferably, about 0.01 µg/kg/day to about 20 µg/kg/day or about 0.01 µg/kg/day to about 10 µg/kg/day or about 0.01 µg/kg/day to about 1 µg/kg/day for human; more preferably, about 0.05 µg/kg/day to about 5 µg/kg/day. In another embodiment, the metallic particles can be administered to a subject in a range from about 0.01 mg/kg/day to about 1,000 mg/kg/day or about 0.01 mg/kg/day to about 500 mg/kg/day or about 0.01 mg/kg/day to about 250 mg/kg/day or about 0.01 mg/kg/day to about 125 mg/kg/day or about 0.01 mg/kg/day to about 100 mg/kg/day or about 0.01 mg/kg/day to about 75 mg/kg/day or 0.01 mg/kg/day to about 50 mg/kg/day or about 0.01 mg/kg/day to about 25 mg/kg/day or 0.01 mg/kg/day to about 10 mg/kg/day; or about 0.01 mg/kg/day to about 5 mg/kg/day preferably, about 0.01 mg/kg/day to 10 mg/kg/day or about 0.01 mg/kg/day to about 5 mg/kg/day or about 0.01 mg/kg/day to about 1 mg/kg/day for human; more preferably, about 0.02 mg/kg/day to 1 mg/kg/day for human.

The desired dose may be presented in a single dose or as divided dose administered at appropriate intervals, for example as two, three, four or more doses per day. While it is possible that, for use in therapy, the compounds may be administered as the raw chemical, it is preferable to present the active ingredient as a pharmaceutical composition. The invention thus further provides a pharmaceutical combination or composition of the metallic nanoparticles or metallic particles as described herein together with one or more pharmaceutically acceptable carriers and, optionally, other therapeutic and/or prophylactic ingredients. The carrier(s) must be "acceptable" in the sense of being compatible with the other ingredients of the formulation and not deleterious to the recipient thereof.

The metallic nanoparticle, or metallic particles or composition thereof of the present disclosure can also be administered to subjects by various methods. For instance, the metallic nanoparticle or metallic particles or composition thereof of the present disclosure can be administered by oral administration (including gavage), inhalation, subcutaneous administration (S.C.), intravenous administration (I.V.), intraperitoneal administration (I.P.), intramuscular administration (I.M.), intranasal administration, and combinations of such modes. In further embodiments of the present disclosure, the metallic nanoparticle or metallic particles or composition thereof of the present disclosure can be administered by topical application (e.g, transdermal patch, ointments, creams, salves, eye drops, and the like). Additional modes of administration can also be envisioned.

In addition, the metallic nanoparticles or metallic particles or compositions thereof of the present disclosure may be administered to localized sites in a subject, such as tissue or vasculature that have suffered from neurological disorder. For instance, the metallic nanoparticles or compositions of the present disclosure may be injected directly into the brain or spinal column of a subject requiring an increase of neurite outgrowth.

The metallic nanoparticles or metallic particles or compositions thereof of the present disclosure may also be utilized for targeted treatment. For instance, in some embodiments, therapeutic compositions may be associated and/or conjugated with targeting agents that are for passing the blood-brain barrier.

In various embodiments, the metallic nanoparticles or metallic particles can be optionally combined with or administered in concert with each other or other agents known to be useful in the treatment of the relevant disease or condition. Thus, in the treatment of ALS, for example, the metallic nanoparticles can be administered in combination with Riluzole (Rilutek), minocycline, insulin-like growth factor 1 (IGF-I), and/or methylcobalamin. In another example, in the treatment of Parkinson's disease, the metallic nanoparticles can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, the metallic nanoparticles can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits including combinations as described herein.

Neurite Outgrowth

The metallic nanoparticles or metallic particles or compositions or combinations thereof of the present disclosure can be used in methods for promoting neurite outgrowth. Particularly, the metallic nanoparticles or metallic particles or compositions or combinations thereof can promote the outgrowth of axons and dendrites. By exposing the neurons to the range of action of the metallic nanoparticles or metallic particles or compositions or combinations thereof, the axons and dendrites increase in length and density and recover by regeneration.

Neurological Diseases

The metallic nanoparticles or metallic particles or compositions or combinations thereof of the present disclosure can be used in methods for treating and/or preventing a neurological disorder. These metallic nanoparticles or metallic particles or compositions or combinations thereof are therefore useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) memory loss, and (v) psychiatric disorders. Non-limiting examples of some of these diseases, conditions, and injuries are provided below.

Examples of neurodegenerative diseases and conditions that can be prevented or treated by promoting neurite outgrowth according to the invention include amyotrophic lateral sclerosis (ALS), trigeminal neuralgia, glossopharyngeal neuralgia, Bell's palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson-plus syndromes (e.g., multiple system atrophy, progressive supranuclear palsy, and corticobasal degeneration), dementia with Lewy bodies, frontotemporal dementia, demyelinating diseases (e.g., Guillain-Barre syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Straussler-Scheinker syndrome (GSS), fatal familial insomnia (FFI), and bovine spongiform encephalopathy (BSE, commonly known as mad cow disease)), Pick's disease, epilepsy, and AIDS dementia complex (also known as HIV dementia, HIV encephalopathy, and HIV-associated dementia).

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, for example, stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the metallic nanoparticles provided herein can be useful as components of culture media for use in culturing nerve cells in vitro.

In another aspect, the invention provides a medical device, comprising metallic nanoparticles or metallic particles or compositions thereof in an amount sufficient to treat and/or prevent a neurological disorder. The invention also provides a method for treating and/or preventing a neurological disorder, the method comprising using a medical device containing an effective amount of metallic nanoparticles in a subject, thereby treating and/or preventing a neurological disorder. Any medical device used in neurological system can be used in the invention. In one embodiment, the medical device is an implantable conduit.

Certain aspects of the invention are described in greater detail in the non-limiting Example that follows.

EXAMPLE

Example 1

Neurite Outgrowth Assay

The gold nanoparticles were provided by GNT Biotech & Medicals Co. (Taipei, Taiwan), and were prepared according to the manufacturing systems and methods disclosed in Taiwan Patent No. 1430858.

The primary cortical neurons were obtained from the embryo of an SD rat that had been pregnant 18 days. Cortical tissue was digested and then plated with minimal essential medium containing 5% fetal bovine serum, 5% horse serum and 5 µg/ml insulin-transferrin-selenium. The cells at a density of $5 \times 10^4$ cells/ml were seeded and cultured in an incubator at 37° C. under 5% $CO_2$. After 3-6 hours, plating medium was replaced with neurobasal medium (2% B27-neurobasal medium containing 0.5 mM glutamate and 12.5 uM glutamine) for cultivation.

The effects of gold nanoparticles added at different developmental stages of neurons were tested. In general, cultured neuronal axon was determined at day in vitro (DIV) 2-3, followed by dendrite determination. Gold nanoparticles at a concentration of 0.5 ppm were added to the primary cortical neurons on the first day (DIV 1), the second day (DIV2) and third day (DIV3), respectively. After the cells were cultured to the sixth day (DIVE), immunofluorescence staining was conducted. Tau and MAP2 were used in the staining to distinguish axons and dendrites (Tau for axons in green and MAP2 for dendrites in red). Compared to the control group (FIG. 1A), gold nanoparticle-treated neurons showed longer and a breater number of branches of axons (green) and dendrites (red). Cell nucleus is stained by DAPI (blue) (FIGS. 1B, C and D).

Figure 2:
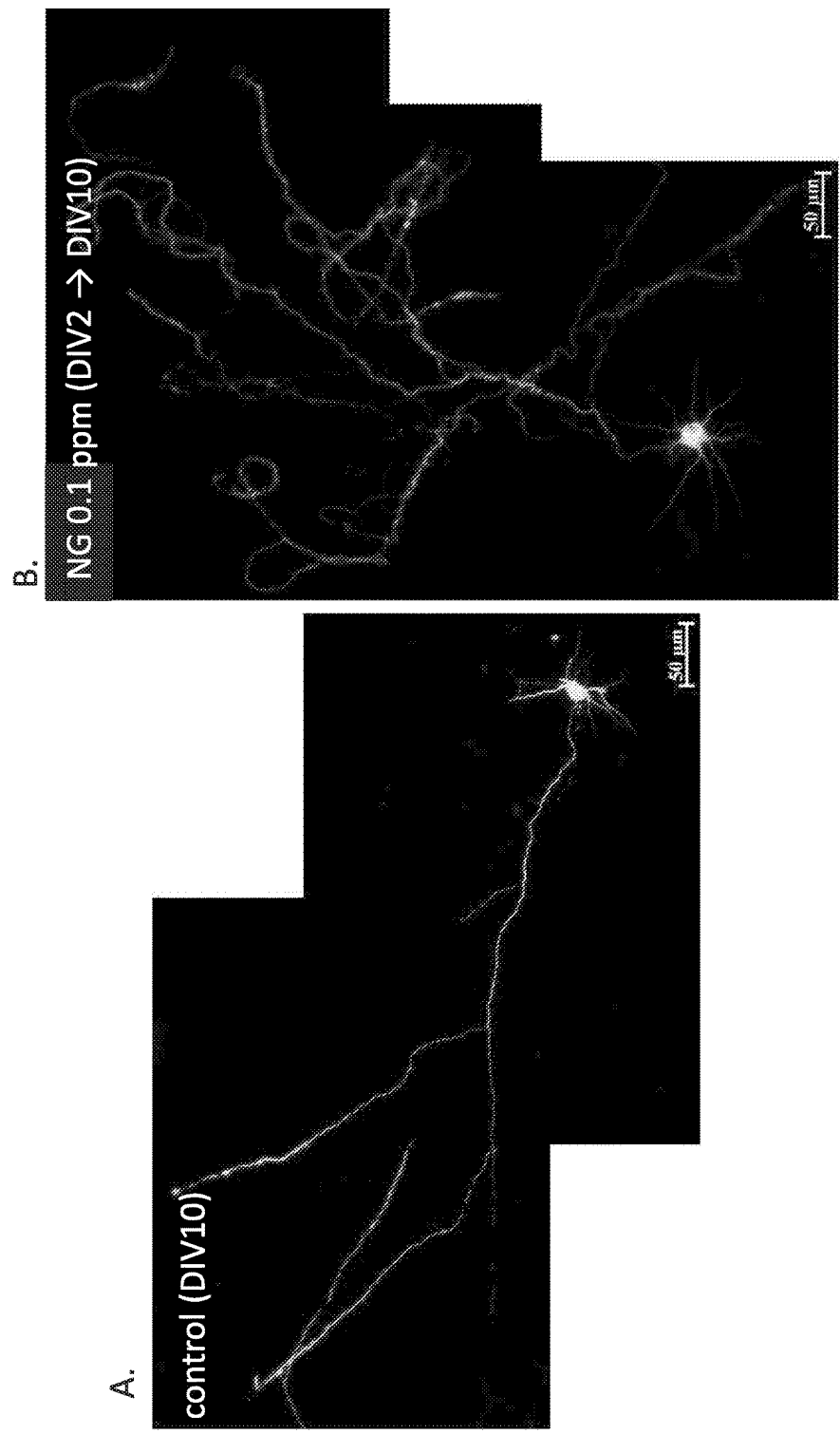
FIGS. 2A to 2D show immunofluorescence staining results of neurite outgrowth assay using 0 (A), 0.1 ppm (B), 0.3 ppm (C) and 0.5 ppm (D) of nanoparticles.
Figure 2:
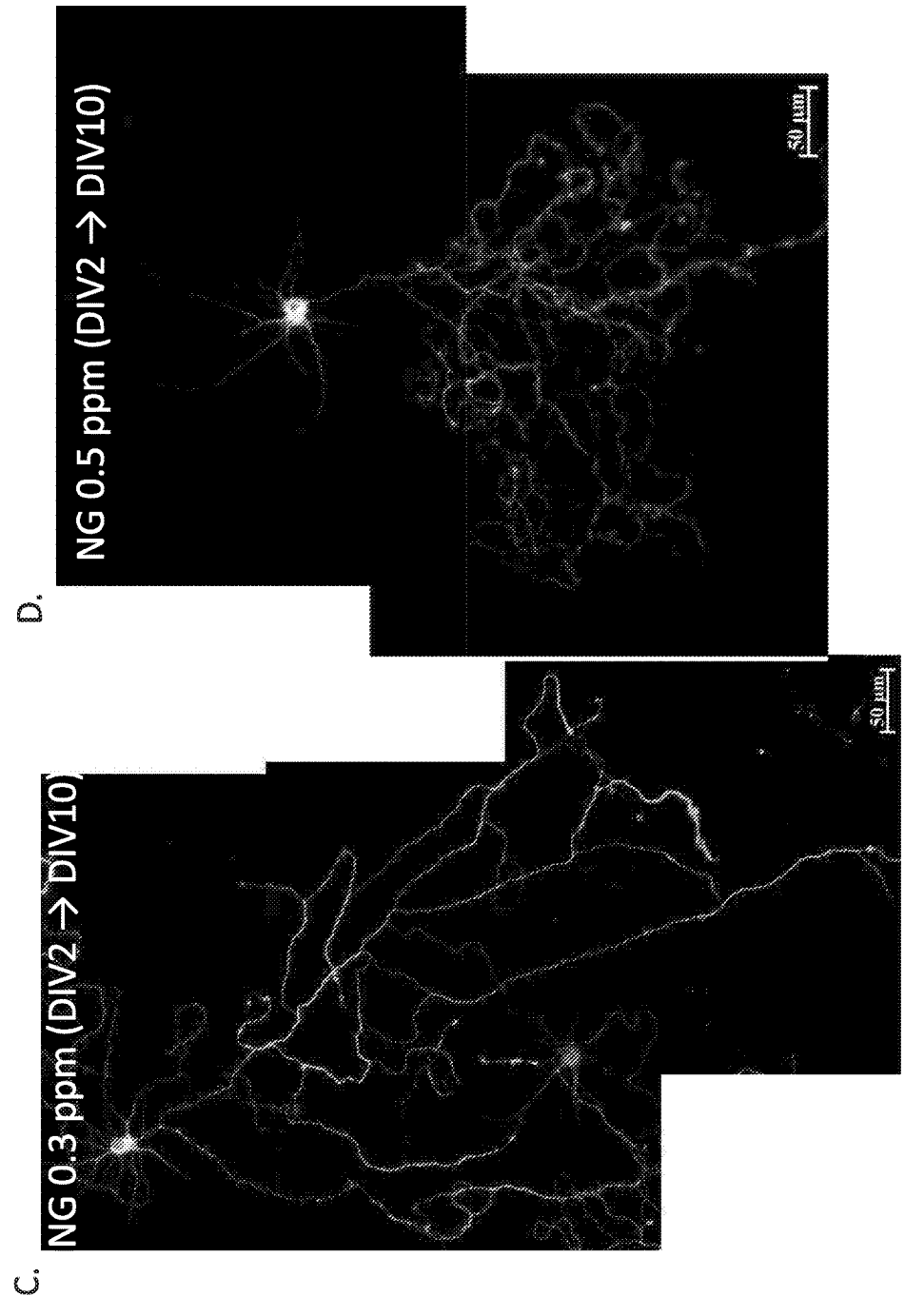

The effects of gold nanoparticles to the outgrowth of neutrites were also evaluated. Gold nanoparticles at concentrations of 0.1 ppm, 0.3 ppm and 0.5 ppm were added to primary cortical neurons at DIV2, respectively. After 8 days of culturing, immunofluorescence staining was conducted. Compared to the control group (FIG. 2A), gold nanoparticles-treated neurons showed longer and more branches of axons (green) and dendrites (red). Cell nucleus is stained by DAPI (blue) (FIGS. 2B, C and D).

Figure 3:
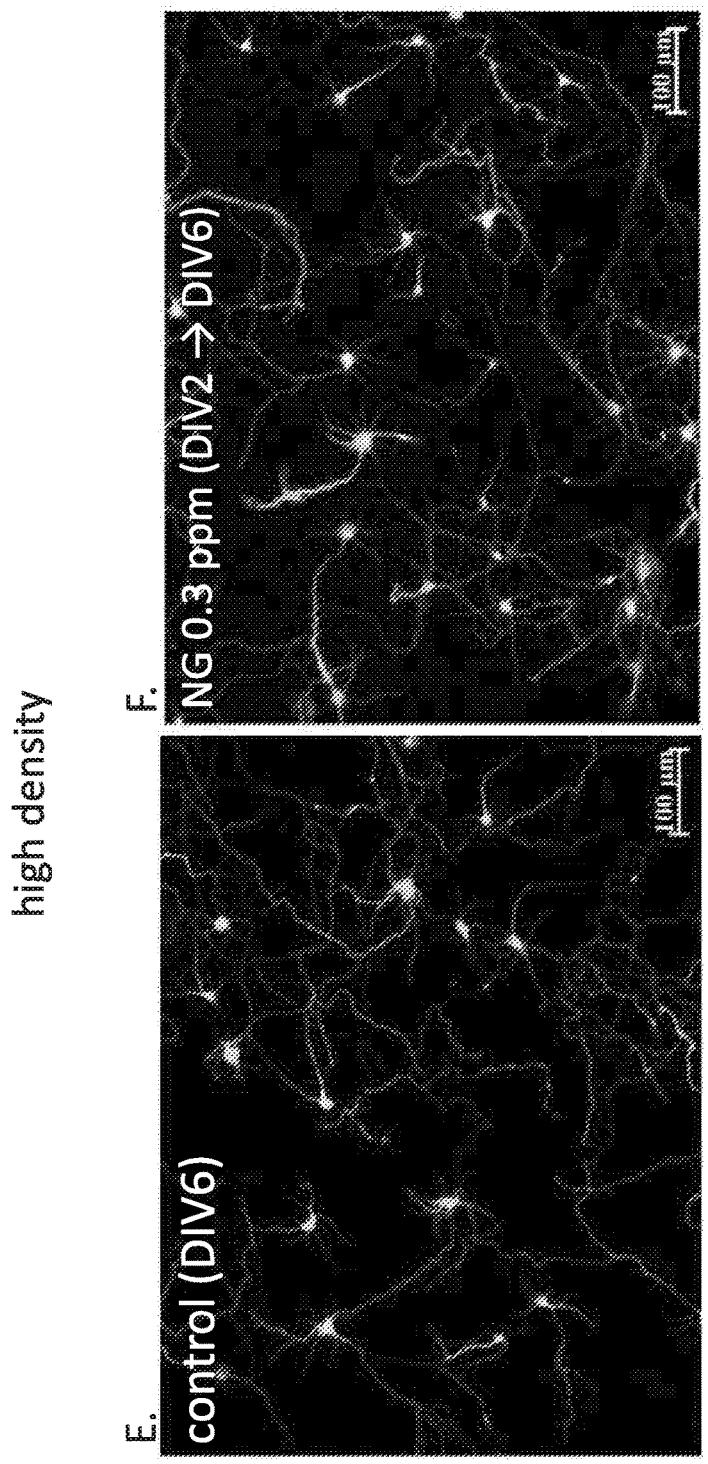
FIGS. 3A to 3F show immunofluorescence staining results of the effects of gold nanoparticles on differentiation of the cells at different cell densities (A: control group (DIV6); B: $5\times10^3$ cells/ml (DIV2-DIV6); C: control group (DIV6); D: $3\times10^4$ cells/ml (DIV2-DIV6); E: $6\times10^4$ cells/ml density (DIV6) and F: $6\times10^4$ cells/ml density (DIV2-DIV6).
Figure 4:
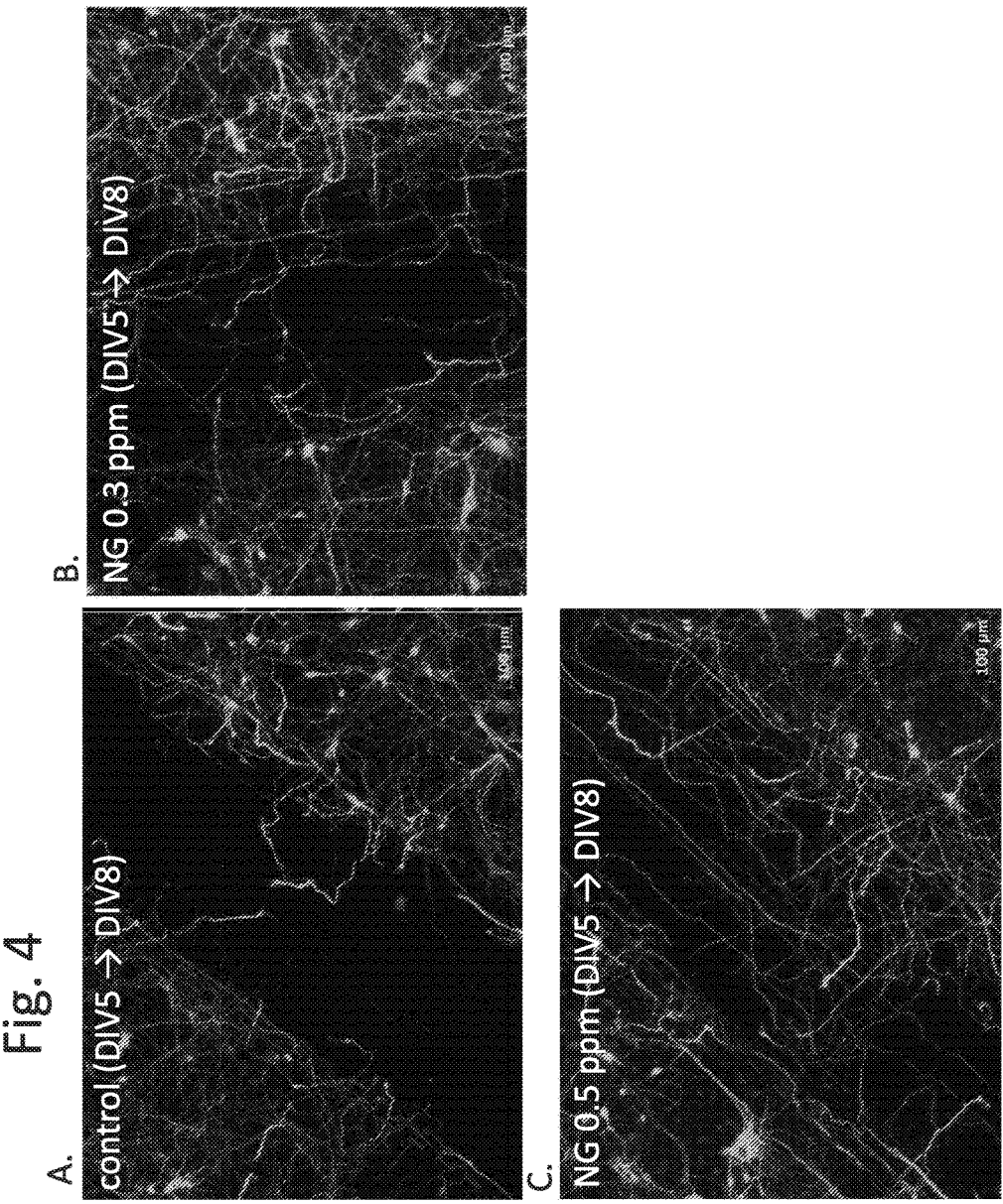
FIGS. 4A to 4C show the results of a scratch test (A: control group; B: the density of the regenerated axons (green) in 0.3 ppm gold nanoparticle-treated group; C: the density of the regenerated axons (green) in 0.5 ppm gold nanoparticle-treated group).

The effects of gold nanoparticles on differentiation of the cells at different cell densities were evaluated. Gold nanoparticles at a concentration of 0.3 ppm were added to the cell samples at the $5\times10^3$ cells/ml, $3\times10^4$ cells/ml and $6\times10^4$ cells/ml densities, respectively. After culturing the cells for 4 days, immunofluorescence staining was conducted. For the cells at the $5\times10^3$ cells/ml (FIG. 3B) and $3\times10^4$ cells/ml (FIG. 3D) densities, compared to the control group (FIGS. 3A and C), the axons (green) and dendrites (red) increased in length and number of branches. Minor changes were observed for the cells at the $6\times10^4$ cells/ml density (FIGS. 3 E and F). The scratch test was used to evaluate the effect of gold nanoparticles in neural regeneration. The primary cortical neurons at a density of $1\times10^6$ cells/ml were cultured to DIV5. A scratch test was conducted. A tip with 200 p was used to mark a cross at the wells of the plate. The culture mediums containing 0.3 ppm and 0.5 ppm gold nanoparticles, respectively, were added to the plate. After culturing for 72 hours, immunofluorescence staining was conducted. The density of the regenerated axons (green) in both 0.3 ppm and 0.5 ppm gold nanoparticles-treated groups (FIGS. 4B and C) increased when compared to the control group (FIG. 4A).

To investigate the effect of nanoparticles in small size, the size of 1 nm to 5 nm of gold nanoparticles at concentrations of 0.5 ppm, 0.75 ppm, 1 ppm and 1.25 ppm were added to primary cortical neurons at DIV2, respectively. After 96 hours of culturing, immunofluorescence staining was conducted. Compared to the control group (375.1 μm average length per axon), 1 nm to 5 nm gold nanoparticles-treated neurons showed longer axons (green) (484.2 μm average length per axon, 491.8 μm average length per axon, 437.2 μm average length per axon and 430.8 μm average length per axon for 0.5 ppm, 0.75 ppm, 1 ppm and 1.25 ppm of gold nanoparticles, respectively). Similarly, the size of 1 nm to 20 nm of gold nanoparticles at concentrations of 0.5 ppm, 0.75 ppm, 1 ppm and 1.25 ppm were added to primary cortical neurons at DIV2, respectively. Compared to the control group (320.2 μm average length per axon), 1 nm to 20 nm gold nanoparticles-treated neurons showed longer axons (green) (412.5 μm average length per axon, 403 μm average length per axon, 467.5 μm average length per axon and 384 μm average length per axon for 0.5 ppm, 0.75 ppm, 1 ppm and 1.25 ppm of gold nanoparticles, respectively).

Figure 5:
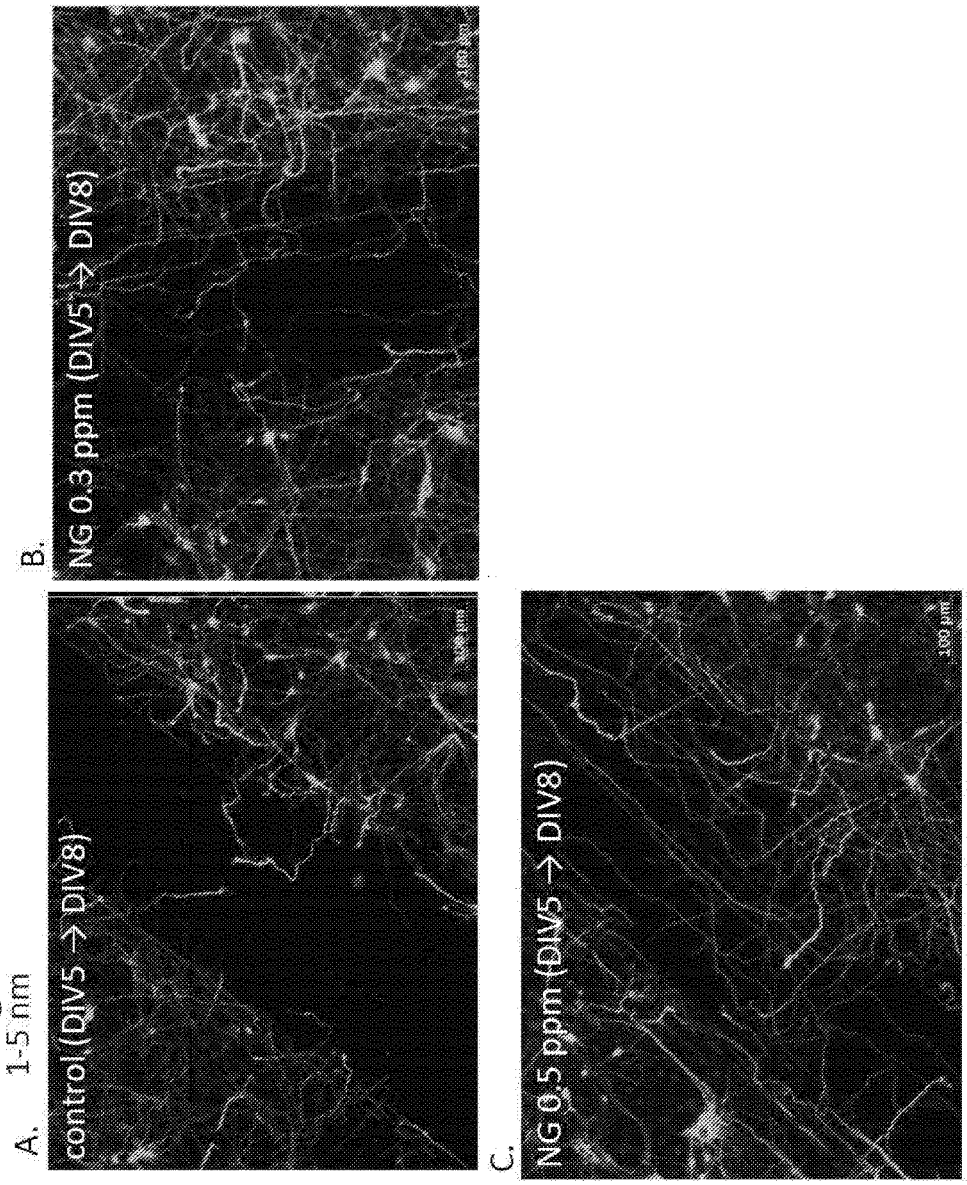
FIGS. 5A to C show the results of the scratch test of the gold nanoparticles having the sizes of 1 nm to 5 nm (A: control group; B: 0.3 ppm of the gold nanoparticles; and C: 0.5 ppm of the gold nanoparticles).
Figure 6:
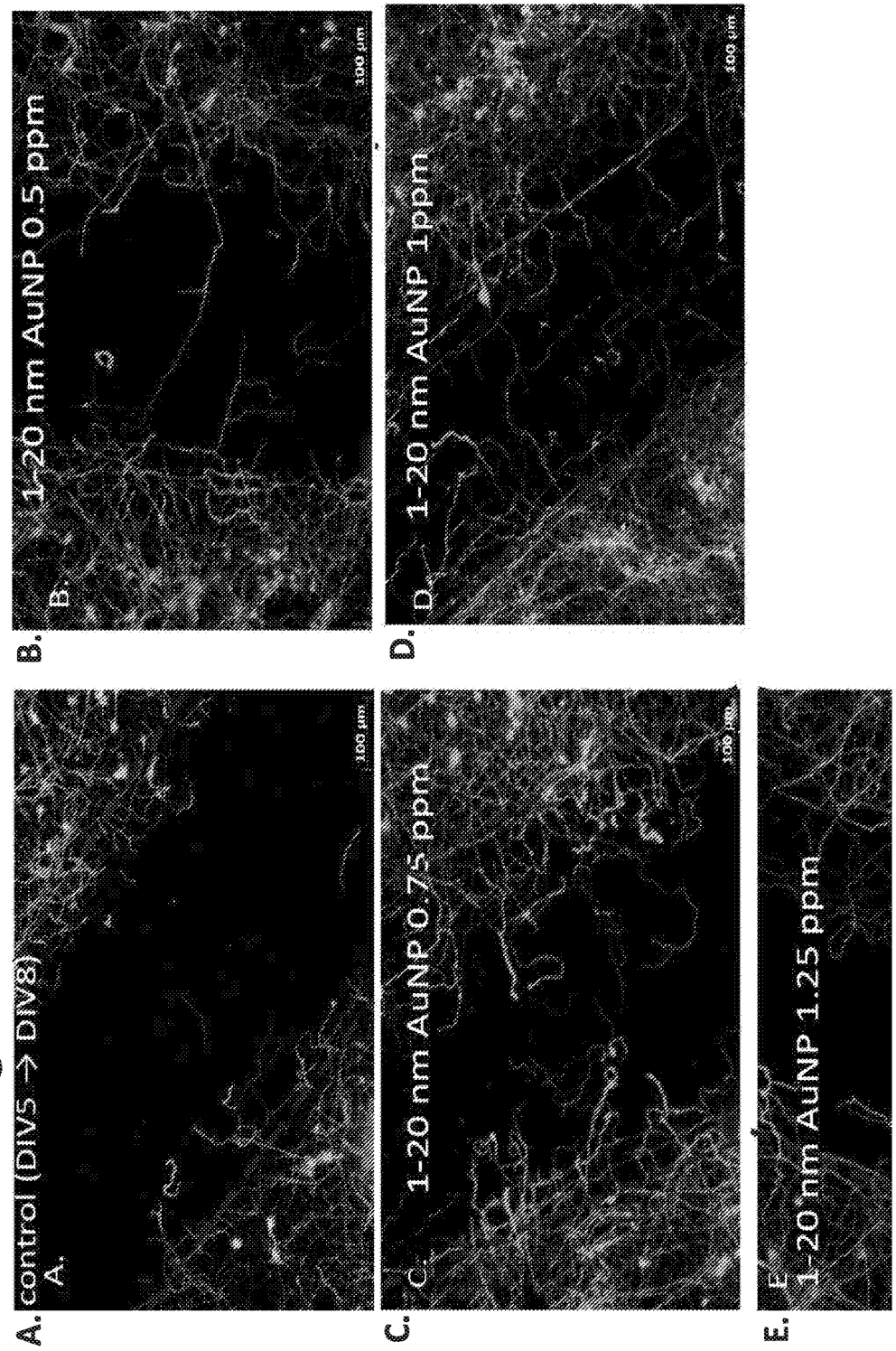
FIGS. 6A to E show the results of the scratch test of the gold nanoparticles having the sizes of 1 nm to 20 nm (A: control group; B: 0.5 ppm of the gold nanoparticles; C: 0.75 ppm of the gold nanoparticles; D: 1.0 ppm of the gold nanoparticlesl and E: 1.25 ppm).

The gold nanoparticles having the sizes of 1 nm to 5 nm and 1 nm to 20 nm were subject to the scratch test as mentioned above. The results show that the gold nanoparticles at the sizes of 1 nm to 5 nm and 1 nm to 20 nm increase the density of regenerated axons (see FIG. 5 for 1 nm to 5 nm gold particles and FIG. 6 for 1 nm to 20 nm gold nanoparticles).

Example 2

Morris Water Maze Task Assay 1 nm to 5 nm of gold nanoparticles were subjected to water maze assay for four days. Twenty SD rats, aged 8 weeks, were used in the assay and divided into two groups (10 rats per group). One group was subjected to intraperitoneal injection (i.p.) with 1 nm to 5 nm of gold nanoparticles (0.5 μg/kg; AuNP group) and one group was subjected to i.p. with PBS (control group) for one month. The administration schedule, administration route and dose are shown in the table below.

| Group | Control | I.P. NG group |
| --- | --- | --- |
| Administration time | Administration three times in a week | |
| Administration route | Intraperitoneal injection (i.p) | |
| Drug concentration | PBS | 0.5 μg/kg |

The water maze method was adopted from that of a previous study (Y. C. Yang, Y. L. Ma, W. T. Liu, and E. H. Lee, "Laminin-beta1 impairs spatial learning through inhibition of erk/mapk and sgk1 signaling, Neuropsychopharmacology, vol. 36, no. 12, pp. 2571-2586, 2011) with modifications. A plastic circular pool 2.0 m in diameter and 0.6 m in height was filled with water (25+/−2° C.) to a depth of 35 cm. A circular platform (20 cm in diameter) was placed at a specific location from the edge of the pool and submerged 2-3 cm below the water surface. Water was made cloudy by adding toxic free dye. Distinctive visual cues were set on the wall. For spatial learning, animals were subjected to 3 trials per day, with one trial early in the morning, one trial at noon, and another in the late afternoon. The training procedure lasted 4 days, and a total of 12 trials were given. This procedure was adopted because spaced training is a better paradigm to facilitate memory consolidation. For these trials, the rats were positioned at different starting points spaced equally around the perimeter of the pool in random order. They had 120 s to find the hidden platform. If a rat could not find the platform, it was guided to the platform and was allowed to remain there for 20 s. The time each animal took to reach the platform was recorded as the escape latency. A probe trial of 120 s was given on day 5 to test their memory retention. The rats were placed in the pool with the platform removed, and the time they spent in each quadrant (Quadrants 1, 2, 3, and 4) was recorded. Quadrant 3 is the target quadrant. For the trained and swimming control experiments, rats in the trained group were subjected to the regular water maze learning procedure.

Figure 7:
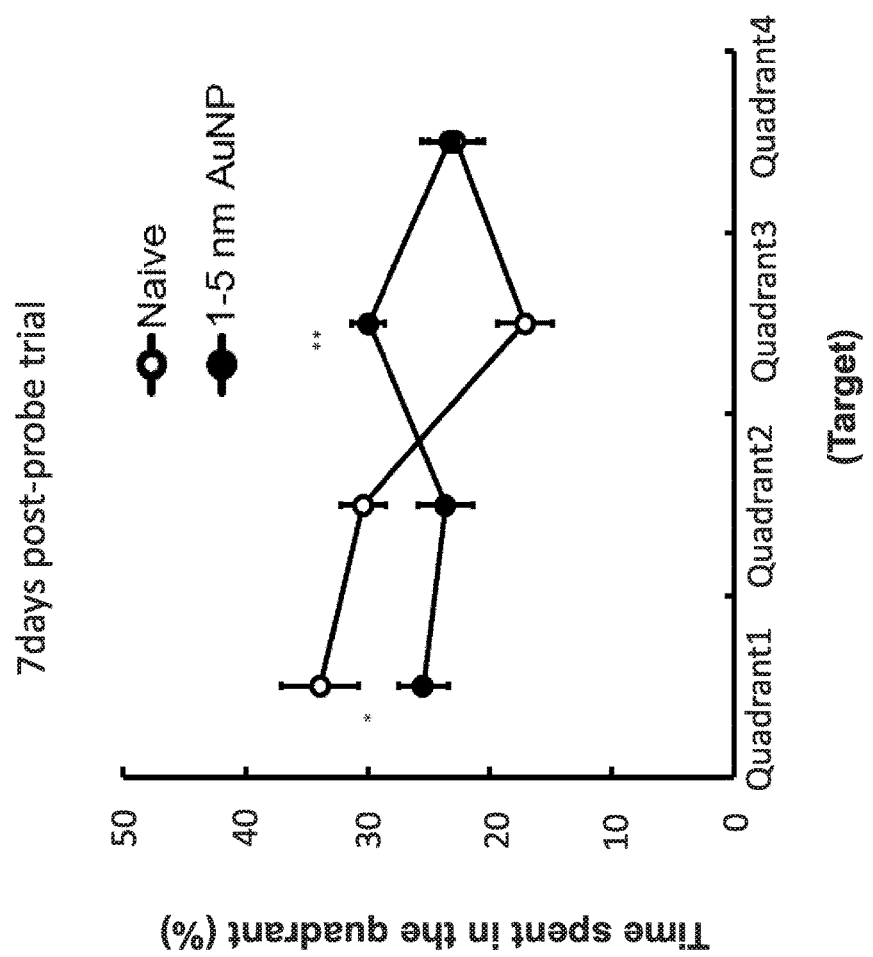
FIGS. 7A to C show the water maze assay of 1 nm to 5 nm of gold nanoparticles (A: the escape latency of the rats in trial days; AuNP group in trial days; B: the escape time they spent in each day quadrant; and C: time spect in the quadrant after 7 days of probe trial).

1 The results show that the AuNP group spent less time to find the platform than control group (see FIG. 7A) and the AuNP group which spent less time to find the platform than control started at the second day (see FIG. 7B). After the fourth day of the trial, the platform was removed and a probe trial was performed. In the AuNP group, the time the rats stopped at the quadrant (platform was removed) is longer than the control group after 7 days of the probe trial (see FIG. 7C).

Figure 8:
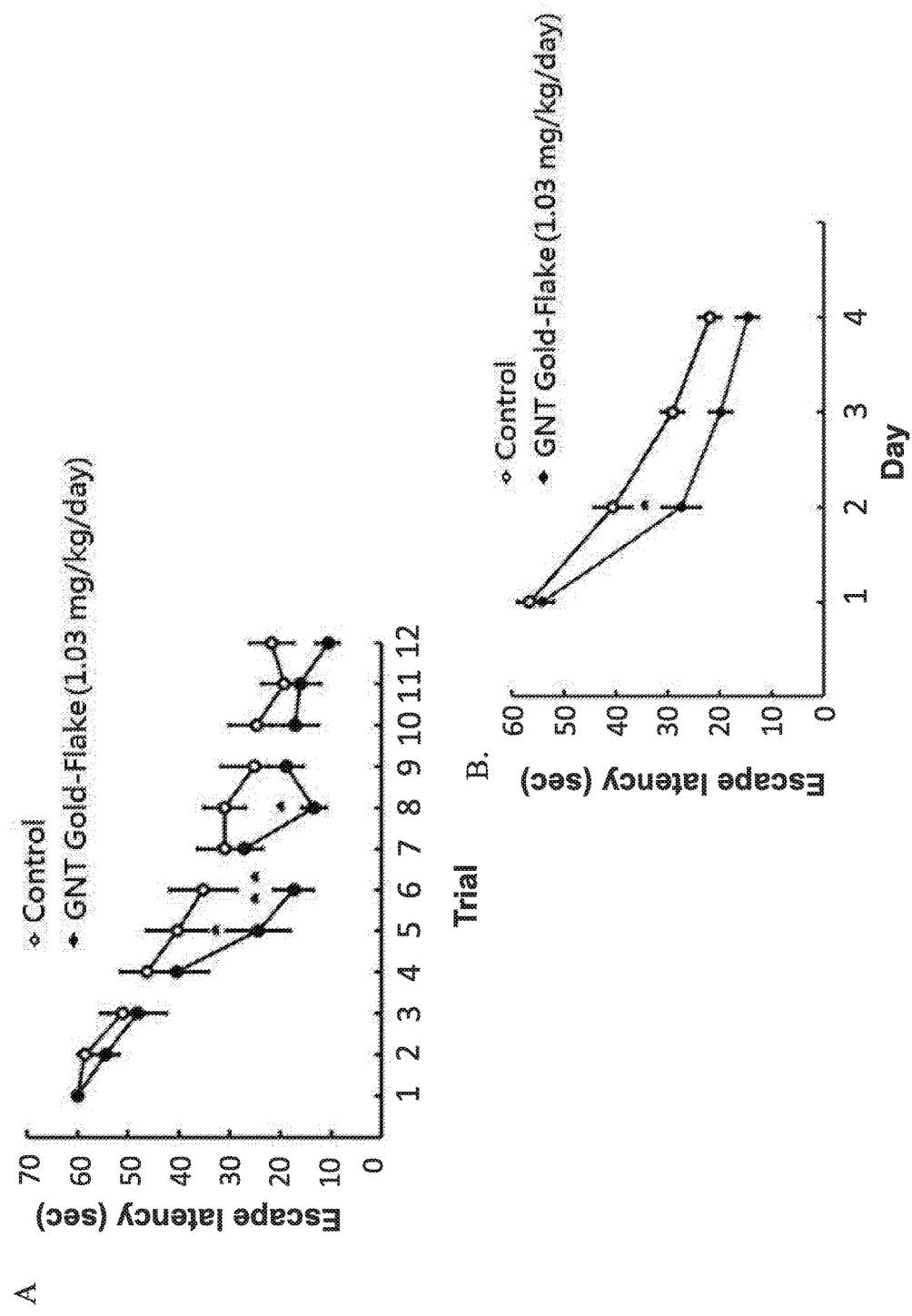
FIGS. 8A and B show the water maze assay of gold particles stacked up with gold nanoparticles of the invention (A: the escape latency of the mices in trial days; B: the escape time they spent in each day).

Furthermore, gold particles stacked up by gold nanoparticles of the invention were subjected to the water maze assay. 1.03 mg/kg/day gold particles were orally administered to mice for two weeks and the results are shown in FIG. 8 (8A and 8B for the escape latency of the mices in trial days and the escape time they spent in each quadrant, respectively).

Example 3

MotorFunction Recovery Assay of the Effect of Gold Nanoparticles on Transected Sciatic Nerve Injury Rat Model Transection of the sciatic nerve, which innervates the hindpaw, is a model of peripheral nerve injury. ICR male mice were randomly divided into four groups (three mice per group). The mice were anesthetized with an agent containing 50% zoletil and 2% rompun. One group of the anesthetized rats was subjected to surgical operation but no sciatic nerves were transected (naïve group). The sciatic nerves of the other three groups of anesthetized rats were transected surgically wherein one group of rats were directly administered with 0.9% NaCl to the sciatic nerves as nerve injury alone control, one group of rats were directly administered to the sciatic nerves topically with 0.5 ppm NG, and one group of mice were administered with 0.5 ppm NG by intraperitoneal injection (i.p.) post-operation (post-OP). The administration schedule is listed in the table below.

| Group | Naïve | Nerve injury | Nerve injury + NG applied topically | Nerve injury + IP NG post-OP |
|---|---|---|---|---|
| Transection of sciatic nerve | No | Yes | Yes | Yes |
| Administration of drug | No | 0.9% NaCl | 0.5 ppm NG | |
| Time of administering drug | No | 0.9% NaCl was immediately added to the transected sciatic nerve topically | intraperitoneal injection (i.p) post-operation | |

Figure 9:
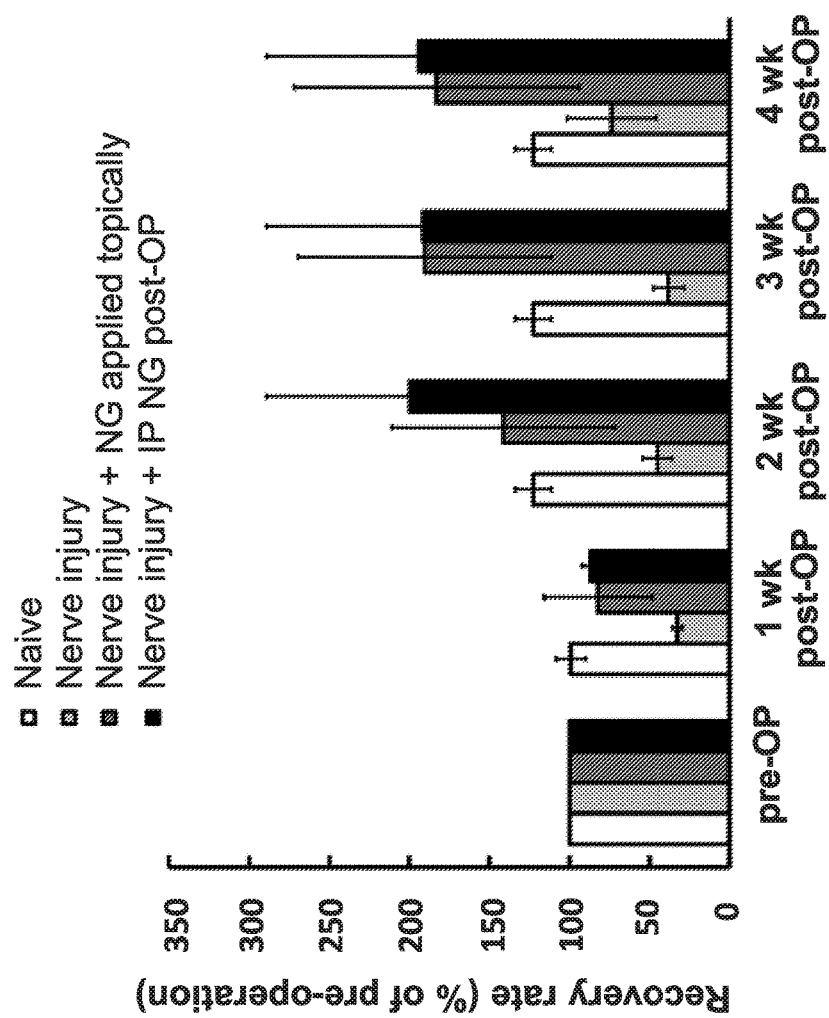
FIG. 9 shows that the motor function of the sciatic nerve injured mice with gold nanoparticle treatment significantly recovered, whereas the sciatic nerve injured control group only slightly recovered after four weeks.

A rotarod performance test was conducted respectively to evaluate the regeneration of the transected sciatic nerves of the mice before and after the surgical operation. The rats were placed on the horizontally oriented, rotating cylinder (rod) of the rotarod at 2 rpm for 5 minutes. Subsequently, the rotarod speed was increased to 20 rpm over 20 minutes and the time that the mice fell to the ground was recorded. The recovery rate is calculated by dividing the time that the mice after surgical operation fell to the ground by the time that the mice before surgical operation fell to the ground. After one week of administration of NG, the motor function of the sciatic nerve injured mice with gold nanoparticles treatment had significantly recovered, whereas the sciatic nerve injured control group showed only slight recovery after four weeks (FIG. 9).

Motor coordination was further tested in transected sciatic nerve injury rats using balance beam test (Metz, G. A. S., et al., Efficient testing of motor function in spinal cord injured rats. Brain Research, 2000. 883(2): p. 165; Cummings, B. J., et al., Adaptation of a ladder beam walking task to assess locomotor recovery in mice following spinal cord injury. Behav Brain Res, 2007. 177(2): p. 232-41). Performance on the beam was quantified by measuring the time it takes for the mouse to traverse the beam. The time taken for the rats to traverse the beam was 18.5 seconds for the naïve group, 14.67 seconds for the nerve injury group, 11.73 seconds for the nerve injury+NG applied topically group and 11.73 seconds for the nerve injury+IP NG post-OP group (see FIG. 10).

Example 4

Novel Object Recognition Test

Novelty object recognition test is a test using a characteristic mouse's preference for novelty, and differs from other evaluation methods of learning in that the test does not use any artificially reinforced factor. The training apparatus was a clear Plexiglas box (48 cm×38 cm×27.5 cm) covered with white masking so that the mouse could not see the surrounding environment. The mouse was placed in a box without stress for 10 minutes for acclimation. After 24 hours, two objects with the same shape and color were placed in the box. The mouse was then placed in the box and allowed to explore the two identical objects for 5 min, and the total time spent and the frequency of exploring both objects were recorded. After 3 hours, the object at the right side of the box was changed to one with a different shape and color than the object on the left side of the box, and then the mouse was placed in the box for 5 minutes. The total time spent and the frequency of exploring both objects were recorded.

After 24 hours, two identical objects, different from those mentioned above, were placed in the box. The mouse was then placed in the box for 5 minutes and the total time spent and the frequency of exploring both objects were recorded. After 24 hours, the object on the right side of the box was changed to one with a different shape and color than the object on the left side of the box, and the mouse was then placed in the box for 5 minutes. The total time spent and the frequency of exploring both objects were recorded.

Example 5

Cell Viability Assay

Cell viability was evaluated by an MTT (3-(4,5-cimethylthiazol-2-yl)-2,5-diphenyl tetrazolium bromide, Sigma-Aldrich) assay 24 h after gold nanoparticle treatment at concentrations of 0, 1, 10, and 100 ppm. Standard MTT assay protocol was performed as known in the art. Cells were incubated with 1 ml of MTT (0.5 mg/mL) reagent (Sigma-Aldrich) and 9 ml of neurobasal medium at 37° C. for 3 h. The MTT solution was removed, and DMSO was added to the wells shaken at room temperature for 1 h. The amount of MTT formazan product was quantified by measuring its absorbance at 570 and 630 nm by using an ELISA plate reader (Lab system multiskan MCC/340, Arges, Romania).

Example 6

Inhibitory Avoidance Learning Task

The apparatus consisted of a trough-shaped alley divided by a sliding door that separates an illuminated safety compartment and a dark compartment. A shock generator that produced current was connected to the floor of the dark compartment (UGO Basile, Comerio VA, Italy). The method used was adopted from that of previous studies with modifications. The behavioral task, including the training and testing procedures, was recorded between 8:00 AM and 6:00 PM. Before the experiment, the rats were habituated in a dim room for 1 h so that they could adjust to the environment. In the training phase, a rat was placed at the far end of the illuminated compartment facing away from the door. As the rat turned around, the door shut, and after 2 s, a 1 mA/s footshock was given twice. The rat was then removed from the alley and returned to its cage. At different times after training (1 d and 7 d later), a retention test was given. Rats were tested after 1 day and 7 days in the same manner as in the training, but without receiving a shock. Testing was terminated either when the rat entered the dark chamber or after 600 s without entry. Rats that did not enter the dark compartment and reached the ceiling score of 600 s were removed from the alley and assigned as rats with good memory. The animals placed in the dark compartment who received footshock (1 mA/s for 2 s) directly were assigned to the footshock-only control group.

Example 7

Step-Down Passive Avoidance Test

Animals were familiarized with the instrument 24 h before training. The next day, rats were placed on the elevated platform situated in the centre of the floor of the passive avoidance test box and the latency to stepping-down was recorded. On the third day of the experiment, immediately after stepping down, animals received mild electric shock (3V, 3 sec duration, D.C.) through the grid floor and then returned to their home cages. On the following day (at 24 h retention interval) rats were placed on the platform again without any electric shock given to them. Latency to stepping-down was recorded. If the rat remained on the platform for 5 mins, it was assigned a maximum score of 300 sec.

Example 8

Sciatic Nerve Function Index (SFI)

Four weeks following sciatic nerve transection, all animals were subjected to a series of weekly motor activity assessments. Recovery of activity was considered proof of adequate post nerve crush reinnervation of the right hind limb, and functional recovery was monitored by analysis of the free-walking pattern. This method describes an index based on measurements of the footprints of walking rats, which provides a reliable and easily quantifiable method of evaluating the functional condition of the sciatic nerve. For this test, the rats were trained to walk over a white sheet of paper covering the bottom of a 100-cm-long, 8.5-cm-wide track, which ended in a dark box. Afterwards, the animals had their plantar hind feet painted with dark dye and were placed on the track to walk. The rat footprints were used to determine the following measurements: distance from the heel to the third toe [print length (PL)], distance from the first to the fifth toe [toe spread (TS)], and distance from the second to the fourth toe [intermediary toe spread (ITS)]. These three measurements were obtained from both the experimental (E) and normal (N) sides of the animal. Several prints of each foot were obtained on each track, but only three prints of each foot were used to determine the mean measurements in the E and N sides. These mean measurements were then included in the SFI formula: SFI0−38.3 (EPL−NPL)/NPL+109.5 (ETS−NTS)/NTS+13.3 (EIT−NIT)/NIT−8.8. The result obtained was considered a functional index of the sciatic nerve, where 0 to −12 represented excellent function, −13 to −99 indicated partial recovery of neurological function, and −100 represented complete deficit of nerve function.

What is claimed is:

1. A method for improving neurite outgrowth, the method consists of exposing the neuron to an extent to which a metallic nanoparticle or a metallic particle formed by stacking up a plurality of the metallic nanoparticles acts to promote neurite outgrowth, wherein the size of the metallic nanoparticle is between 1 nm and 20 nm.

2. The method of claim 1, wherein the metallic nanoparticle is selected from the group consisting of silver nanoparticles, gold nanoparticles, platinum nanoparticles, palladium nanoparticles, aluminum nanoparticles, nickel nanoparticles, cobalt nanoparticles, copper nanoparticles, and combinations thereof.

3. The method of claim 1, wherein the metallic nanoparticle or metallic particle is a gold nanoparticle or particle.

4. The method of claim 1, wherein the metallic nanoparticle or metallic particle is combined with a targeting agent passing the blood-brain barrier.

5. The method of claim 1, wherein the metallic nanoparticle or metallic particle can be optionally combined (and/or conjugated) with a second therapeutic agent that can pass the blood-brain barrier.

6. The method of claim 1, wherein the neuron is an injured neuron.

7. The method of claim 1, wherein the outgrowth of the neurite is for axon and/or dendrite outgrowth.

8. The method of claim 1, wherein the neurite is in vivo or in vitro.

9. The method of claim 1, wherein the subject is a human.

10. The method of claim 1, wherein the neuron forms part of a nerve graft or a nerve transplant.

* * * * *